United States Patent [19] [11] 4,218,457
Atsumi et al. [45] Aug. 19, 1980

[54] 2-SUBSTITUTED 5-HYDROXY-1H-IMIDAZOLE-4-CARBOXA- MIDE DERIVATIVES AND USE

[75] Inventors: Toshio Atsumi, Ashiya; Yuzo Tarumi, Nishinomiya; Noboru Yoshida, Saitama, all of Japan

[73] Assignee: Sumitomo Chemical Company, Limited, Osaka, Japan

[21] Appl. No.: 940,131

[22] Filed: Sep. 6, 1978

[30] Foreign Application Priority Data

Sep. 6, 1977 [JP] Japan .................. 52-107641
Oct. 17, 1977 [JP] Japan .................. 52-124992
Oct. 17, 1977 [JP] Japan .................. 52-124995
Mar. 13, 1978 [JP] Japan .................. 53-28900

[51] Int. Cl.$^2$ .................. A61K 31/415; A61K 31/44; C07D 233/32; C07D 403/04
[52] U.S. Cl. .................. 424/263; 424/273 R; 546/278; 548/301
[58] Field of Search .................. 548/301; 424/273 R, 424/263; 546/278

[56] References Cited

U.S. PATENT DOCUMENTS 3,772,319  11/1973  Heyes et al. .................. 548/301
4,140,788   2/1979  Atsumi et al. .................. 548/301

OTHER PUBLICATIONS

Cunningham et al. Immunology 1968, vol. 14, 559–(facing 600).
Miller et al. J. Amer. Chem. Soc. 1952, vol. 74, pp. 2892–2894.
Mizuno et al. J. of Antibiotics 1974, vol. 27, pp. 775–782.
Sakaguchi et al. J. of Antibiotics 1975, vol. 28, pp. 798–803.
Atsumi et al. Chem. Abst. 1977, vol. 86, No. 106582g.
Sakaguchi et al. Cancer Research 1975, vol. 35, pp. 1643–1648.
Sakaguchi et al. Proceedings of the First Intersectional Congress of IAMS 1974, vol. 3, pp. 539–541.
Schipper et al. J. Amer. Chem. Soc. 1952, vol. 74, pp. 350–353.
Atami et al. Chem. Abst. 1978, vol. 88, No. 105334g.
Tsujino et al. Proceedings of the First Intersectional Congress of IAMS 1974, vol. 3, pp. 441–443.

Primary Examiner—Natalie Trousof
Attorney, Agent, or Firm—Wenderoth, Lind & Ponack

[57] ABSTRACT

Compounds of the formula, $$H_2N-\underset{\underset{HO}{|}}{\overset{\overset{O}{\|}}{C}}-\underset{\underset{H}{N}}{\overset{N}{=}}R \quad (I)$$

wherein R is $C_2$-$C_{17}$ alkyl group, $C_3$-$C_7$ cycloalkyl group, 1-adamantyl group, pyridyl group, pyridine N-oxide, diphenylmethyl group, benzyl group which may or may not be substituted with nitro group, halogen atom, $C_1$-$C_3$ alkyl group or $C_1$-$C_3$ alkoxy group, or phenyl group which may or may not be substituted with nitro group, halogen atom, hydroxy group, $C_1$-$C_3$ alkyl group, $C_1$-$C_3$ alkoxy group, carboxy group, $C_2$-$C_4$ alkoxycarbonyl group, phenoxycarbonyl group, carbamoyl group, N-phenylcarbamoyl group, N-adamantylcarbamoyl group, benzoylamino group, trifluoromethyl group, $C_2$-$C_4$ alkanoyloxy group, 1-adamantoyloxy group or benzoyloxy group and salts thereof have an anticancer activity and an immunostimulating activity.

26 Claims, No Drawings

2-SUBSTITUTED 5-HYDROXY-1H-IMIDAZOLE-4-CARBOXAMIDE DERIVATIVES AND USE

The present invention relates to novel 2-substituted 5-hydroxy-1H-imidazole-4-carboxamide derivatives and their pharmaceutically acceptable salts, which have now been found to be useful as anticancer agents and immunostimulants, and to their preparation and use.

2-Substituted 5-hydroxy-1H-imidazole-4-carboxamide derivatives provided by the present invention are represented by the formula,

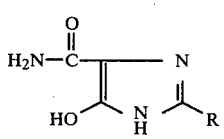 (I)

wherein R is $C_2-C_{17}$ alkyl group, $C_3-C_7$ cycloalkyl group, 1-adamantyl group, pyridyl group, pyridine N-oxide, diphenylmethyl group, benzyl group which may or may not be substituted with nitro group, halogen atom, $C_1-C_3$ alkyl group or $C_1-C_3$ alkoxy group, or phenyl group which may or may not be substituted with nitro group, halogen atom, hydroxy group, $C_1-C_3$ alkyl group, $C_1-C_3$ alkoxy group, carboxy group, $C_2-C_4$ alkoxycarbonyl group, phenoxycarbonyl group, carbamoyl group, N-phenylcarbamoyl group, N-adamantylcarbamoyl group, benzoylamino group, trifluoromethyl group, $C_2-C_4$ alkanoyloxy group, 1-adamantoyloxy group or benzoyloxy group.

As used herein, the term "$C_2-C_{17}$ alkyl" means a straight or branched alkyl having 2 to 17 carbon atoms such as ethyl, n-propyl, iso-propyl, n-butyl, iso-butyl, tert-butyl, and n-heptadecyl. The term "$C_3-C_7$ cycloalkyl" means a cycloalkyl having 3 to 7 carbon atoms (i.e. cyclopropyl, cyclobutyl, cyclopentyl, cyclohexyl or cycloheptyl). The term "halogen" includes fluorine, chlorine, bromine and iodine. The term "$C_1-C_3$ alkyl" means an alkyl having 1 to 3 carbon atoms (i.e. methyl, ethyl, n-propyl or iso-propyl). The term "$C_1-C_3$ alkoxy" means an alkoxy having 1 to 3 carbon atoms (i.e. methoxy, ethoxy, n-propoxy or iso-propoxy). The term "$C_2-C_4$ alkoxycarbonyl" means an alkoxycarbonyl having 2 to 4 carbon atoms (e.g. ethoxycarbonyl, n-propoxycarbonyl or isopropoxycarbonyl). The term "$C_2-C_4$ alkanoyloxy" means an alkanoyloxy having 2 to 4 carbon atoms such as acetoxy or propionyloxy.

The compounds (I) of the present invention can be prepared by reacting imidoester derivatives of the formula,

 (II)

wherein R is as defined above, and Y is lower alkoxy, phenoxy, benzyloxy or benzylthio group, or its salts with α-aminomalonamide.

It is preferable to carry out the reaction using a solvent, though the reaction proceeds smoothly without a solvent.

Examples of suitable solvent used in this reaction are alcohols such as methanol or ethanol, ethers such as ethyl ether, tetrahydrofuran, dioxane or dimethoxyethane, aromatic hydrocarbons such as benzene, toluene or xylene, chlorinated lower aliphatic hydrocarbons solvent such as carbontetrachloride, chloroform, dichloromethane or dichloroethane, and other organic solvents such as dimethylformamide, acetonitrile, dimethylsulfoxide or acetamide. Among these solvents, alcohols are the most preferable.

This reaction may preferably be carried out at a temperature ranging from 0° to 100° C.

With respect to the imidoester derivatives (II), those of which Y is lower alkoxy are particularly suitable for this process.

Examples of preferred salts of the imidoester derivatives (II) are hydrochlorides. Generally speaking, the imidoester derivatives (II) may be used in their free form of salt form in this process. However, when the imidazole derivatives of the formula (I) wherein R is pyridyl group, pyridine N-oxide group, or phenyl group substituted with an electron-withdrawing group such as nitro group are to be prepared, the free imidoester derivatives should be used.

When the free imidoester derivatives (II) are used, the reaction is carried out in the presence of acids in order to neutralize ammonia liberated during the reaction.

The salts of the imidoester derivatives can conventionally be prepared from the corresponding nitrile derivatives.

The free imidoester derivatives can be obtained by the method disclosed by Schaefer et al. (Fred. C. Schaefer et al., J. Org. Chem., 20, 412 (1961)).

When thus obtained free imidoester derivatives are used without isolation, the amount of acids has to be increased to neutralize both ammonia liberated during the reaction and sodium methoxide which is used for the preparation of the free imidoester derivatives.

Examples of acids used in this process are such organic acids as acetic acid, and arylsulfonic acids (e.g. p-toluenesulfonic acid, benzenesulfonic acid) and inorganic acids such as hydrochloric acid or sulfuric acid.

The compounds of the formula (I) can also be prepared by reacting α-aminomalonamide with ortho ester derivatives of the formula,

 (III)

R—C(OZ)₃ wherein R is as defined above, and Z is lower alkyl.

This reaction can be carried out under the same reaction conditions as those of the reaction of the imidoester derivatives (II) or their salts.

The reaction can be conducted at a temperature ranging from 0° to 100° C., preferably, in such solvents as mentioned above.

However, it is preferable to carry out the reaction in the presence of a catalyst, for example, such acids as mentioned above.

With respect to the ortho ester derivatives (III), the derivatives wherein Z is methyl or ethyl are preferable.

The compounds of the formula (I) wherein R is phenyl group substituted with hydroxy group can be obtained by conducting the alcoholysis of the compounds of the formula (I) wherein R is phenyl group substituted with benzoyloxy group with methyl alcohol in the presence of sodium methoxide.

The free compounds of the present invention can be obtained by a conventional method from the corresponding salts. For example, they can be obtained by neutralizing the salts of the compounds of the formula (I) with an aqueous solution of inorganic bases or by reacting them with bases in an organic solvents.

Examples of suitable bases are sodium hydroxide, potassium hydroxide, sodium carbonate, sodium bicarbonate, potassium carbonate and potassium bicarbonate.

The compounds of the present invention have a potent anticancer activity and a low toxicity. They also have a potent immunostimulating activity. For example, they have been found to have a potent anticancer activity against experimental mouse tumors such as Sarcoma 180, and a potent immunostimulating effect on immunosuppressed mice as shown in the following Table I and Table II.

The anticancer activities of the compounds of the present invention were estimated according to the methods described in "Oyo-Yakuri" vol. 4, p. 521 (in Japanese). The results are given in the following Table I.

Thus, the compounds were dissolved or suspended in saline before use, and their anti-tumor activities were tested against Sarcoma 180. Triethylenethiophosphoramide (TESPA) was used as a positive control drug.

Seven ICR-JCL male mice (6 weeks old, weighing 23–26 g) were used for a group. $2 \times 10^6$ ascitic tumor cells were transferred subcutaneously at the inguinal region of the mouse. At the day 9 after tumor transplantation, the mice were killed and tumors were removed and weighed. The inhibition ratio (IR) was obtained by comparing the tumor weights of the test group with those of the control group. The test compounds were administered intraperitoneally once a day for 7 days. The treatment was begun from 24 hours after tumor transplantation.

$$IR = \left(1 - \frac{\text{the mean tumor weights of treated group}}{\text{the mean tumor weights of control group}}\right) \times 100;$$

Table I

| | Compounds | | Dosage mg/kg/day | Route | Inhibition ratio (%) Sarcoma 180 (solid) |
|---|---|---|---|---|---|
| A | R : $C_2H_5-$ | | 200 × 5 | ip | 34.4 |
| B | : $-CH_2-$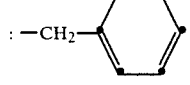 | | 171 × 5 | ip | 31.0 |
| C | :  | | 100 × 5 | ip | 50.2 |
| D | : 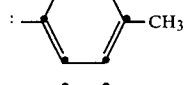$-NO_2$ | | 195 × 5 | ip | 33.0 |
| E | : $C_{17}H_{35}-$ | | 288 × 5 | ip | 34.9 |
| F | : 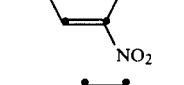$-CH_3$ | | 171 × 5 | ip | 31.5 |
| G | : 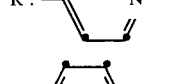 $NO_2$ | | 196 × 5 | ip | 33.4 |
| H | R : 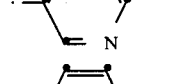 | | 100 × 5 | ip | 50.3 |
| I | : 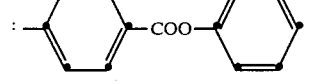 | | 100 × 5 | ip | 48.7 |
| J | : 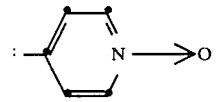 | | 50 × 7 | ip | 32.1 |
| K | : (N→O pyridine) | | 100 × 5 | ip | 46.2 |

Table I-continued

| | Anticancer effects on experimental mouse tumors | | |
|---|---|---|---|
| Compounds | Dosage mg/kg/day | Route | Inhibition ratio (%) Sarcoma 180 (solid) |
| L  :—⟨phenyl⟩—F | 50 × 7 | ip | 30.1 |

The immunostimulating activities of the compounds of the present invention are given in the following Table II. Corticosterone, 25 mg/kg, was administered orally to mice once a day on days −2 and −1, after two days a sheep red blood cell preparation (SRBC) was injected in the mice and the compounds were injected subcutaneously once a day on days 0 and 1. The plaque forming cell (PFC) number was measured on day 4 by the Cunningham method. [Cunningham A. J. et al., Immunology, 14, 599 (1968)]

Thus, 4 pieces of 'double-sided' tape (Scotch brand No. 410 double-sided tape), each ¼ in. wide, are laid across a clean microscope slide (75×25 mm) dividing it into three equal areas. Three pre-cleaned coverslips (22 mm square) are pressed firmly on to the tape to form three shallow chambers. A mixture is made at room temperature of the lymphoid cells under test, together with complement (1:10 final dilution of pooled guinea-pig serum), and erythrocytes of the type used for immunization (at a final concentration of about $4 \times 10^8$/ml). When this mixture is applied with a pipette to the side of the chambers, the narrow space between slide and coverslip fills readily by capillarity, and the chambers are sealed with heated paraffin—'Vaseline.' Cells settle to the bottom of the chamber to form a monolayer which is stable provided the slides are kept approximately horizontal. For counting cells producing 7S antibody, antiglobulin serum may be added to the initial mixture at appropriate concentrations. A maximum number of plaques can usually be counted at low magnification after 30 minutes incubation. Slides may be made up in advance and stored ready for use.

Table II

| Compound (I) | | Immunostimulating effect on mouse | | |
|---|---|---|---|---|
| | | Dosage mg/kg/day s.c. | Effect PFC/spleen × 10⁻ | Enhance (%) |
| A: | R = —⟨phenyl⟩—OCO—⟨adamantyl⟩ | 50 | 51.00 ± 6.63 | 80.1 |
| B: | R = —⟨phenyl⟩—Cl | 50 | 37.88 ± 3.64 | 33.8 |
| | Control | | 28.31 ± 4.16 | |
| C: | R = —CH₂—⟨phenyl⟩—OCH₃ | 25 | 69.38 ± 9.97 | 151.1 |
| | Control | | 27.63 ± 2.70 | |
| D | —⟨phenyl⟩—OCH₃ | 50 | 37.63 ± 5.81 | 68.8 |
| E | —⟨phenyl⟩—CONH—⟨adamantyl⟩ | 50 | 50.63 ± 11.28 | 117.1 |
| F | —⟨phenyl⟩—F | 50 | 65.50 ± 13.50 | 193.8 |
| | Control | | 22.29 ± 1.91 | |

Further, they did not show any toxic symptoms symptomus, when over 1000 mg/kg of them were orally administered to mice.

Thus, the compounds of the present invention can be used in therapy for of cancer, collagen disease, rheumatoid arthritis, bronchial asthma, virus infections, bacterial infections and vermination.

Among the compounds of the present invention, the compounds of the formula (I) wherein R is benzyl group substituted with $C_1$-$C_3$ alkoxy group, or phenyl group substituted with halogen atom, $C_1$-$C_3$ alkoxy group, N-adamantylcarbamoyl group or 1-adamantoyloxy group are particularly preferable in view of their excellent immunostimulatory properties.

The compounds of the present invention can be administered orally or parenterally at a daily dose of 2 mg to 200 mg/kg as an immunostimulant and an anticancer agent in a conventional dosage unit form. For the oral or parenteral administration, they are made up alone or together with a conventional pharmaceutical carrier or diluent to a conventional solid or liquid pharmaceutical preparation (e.g. powders, granules, tablets, capsules, suspensions, emulsions, solutions) using the conventional methods in the pharmaceutical field.

The following examples are given to illustrate the present invention more precisely, but it is not intended to limit the present invention thereto.

EXAMPLE 1

To a chilled solution of ethyl iminophenylacetate hydrochloride (5.99 g) in anhydrous methanol (80 ml) was added aminomalonamide (3.51 g). The mixture was stirred for 1 hour at 0°–5° C. and then 3 hours under reflux. After cooling the mixture to 0°–5° C., the precipitated product was filtered and washed with ethanol, isopropylether to give 2-benzyl-5-hydroxy-1H-imidazole-4-carboxamide (4.52 g).
 (i) m.p. 256°–260° C. (dec.)
 (ii) Elemental analysis
 Calculated for $C_{11}H_{11}N_3O_2$: C 60.82%; H 5.10%; N 19.35%;
 Found—:C 60.5%; H 5.2%; N 19.4%.

EXAMPLE 2

To a solution of ethyl imino p-methoxyphenylacetate hydrochloride (8.27 g) in anhydrous methanol (80 ml) was added aminomalonamide (3.51 g), and this mixture was stirred for 0.5 hour at 0°–5° C. and for 2 hours under reflux. After cooling the reaction mixture to 0°–5° C., the precipitated product was separated by filtration, washed with ethanol, isopropylether and dried under vacuum to give 2-(4-methoxybenzyl)-5-hydroxy-1H-imidazole-4-carboxamide (4.95 g). Recrystallization from aqueous methanol gave colorless crystals in the form of fine columns.
 (i) m.p. 270.5°–271.5° C. (dec.)
 (ii) Elemental analysis
 Calculated for $C_{12}H_{13}N_3O_3$: C 58.29%; H 5.30%; N 17.00%;
 Found: C 58.13%; H5.08%; N 16.80%.

EXAMPLE 3

To a chilled solution of ethyl iminobenzoate hydrochloride (18.57 g) in anhydrous methanol (250 ml) was added aminomalonamide (11.71 g). The mixture was stirred for a half hour at 0°–5° C. and then 1 hour under reflux. After cooling to 0°–5° C. again, the precipitated product was filtered and washed with ethanol, isopropylether to give 2-phenyl-5-hydroxy-1H-imidazole-4-carboxamide (11.81 g).
 (i) m.p. 260°–270° C. (dec.)
 (ii) Elemental analysis
 Calculated for $C_{10}H_9N_3O_2 \cdot \frac{1}{2}H_2O$: C 58.46%; H 4.54%; N 20.45%.
 Found: C 58.4%; H 4.6%; N 20.7%.

EXAMPLE 4

To a chilled solution of ethyl imino p-fluorobenzoate hydrochloride (7.33 g) in anhydrous methanol (80 ml) was added aminomalonamide (3.51 g), and this mixture was stirred for 0.5 hour at 0°–5° C. and for 2 hours under reflux. After cooling the reaction mixture to 0°–5° C., the precipitated product was separated by filtration, washed with ethanol, isopropylether and dried under vacuum to give 2-(4-fluorophenyl)-5-hydroxy-1H-imidazole-4-carboxamide (2.98 g).
 (i) m.p. 315°–318° C. (dec.)
 (ii) Elemental analysis
 Calculated for $C_{10}H_8N_3FO_2$: C 54.30%; H 3.65%; N 19.00%.
 Found: C 54.4%; H 3.7%; N 19.0%.

EXAMPLE 5

To a chilled solution of ethyl imino p-chlorobenzoate hydrochloride (5.283 g) in anhydrous methanol (50 ml) was added aminomalonamide (2.342 g) and the mixture was stirred for 0.5 hour at 0°–5° C. and for 2 hours under reflux. After cooling to 0°–5° C. again, the precipitated product was separated by filtration, washed with ethanol, isopropylether and dried under vacuum to give 2-(4-chlorophenyl)-5-hydroxy-1H-imidazole-4-carboxamide (2.415 g).
 (i) m.p. 308°–311.5° C. (dec.)
 (ii) Elemental analysis
 Calculated for $C_{10}H_8O_2N_3Cl$: C 50.54%; H 3.40%; N 17.68%; Cl 14.92%.
 Found: C 50.2%; H 3.4%; N 17.8%; Cl 14.68%.

EXAMPLE 6

To a solution of ethyl imino p-(1-adamantoyloxy)benzoate hydrochloride (1.42 g) in anhydrous methanol (12 ml) was added aminomalonamide (730 mg), and this mixture was stirred for 0.5 hour at 0°–5° C. and for 3 hours under reflux. After cooling the reaction mixture to 0°–5° C. again, the precipitated crystals were separated by filtration, washed with ethanol, isopropylether and dried under vacuum to give 2-[4-(1-adamantoyloxy)-phenyl]-5-hydroxy1H-imidazole-4-carboxamide (430 mg).
 (i) m.p. 278°–279° C.
 (ii) Elemental analysis
 Calculated for $C_{21}H_{23}N_3O_4 \cdot \frac{1}{2}H_2O$: C 64.60%; H 6.20%; N 10.76%.
 Found: C 64.6%; H 6.0%; N 10.8%.

EXAMPLE 7

To a solution of ethyl imino p-[N-(1-adamantyl)carbamoy] benzoate hydrochloride (3.17 g) in anhydrous methanol (50 ml) was added aminomalonamide (930 mg), and this mixture was stirred for 0.5 hour at 0°–5° C. and for 3 hours under reflux. After cooling the reaction mixture to 0°–5° C. again, the precipitated product was separated by filtration, washed with ethanol, isopropylether and dried under vacuum to give 2-{4-[N-(1-adamantyl)carbamoyl]-phenyl}-5-hydroxy-1H-imidazole-4-carboxamide (1.18 g).
 (i) m.p. 298°–303° C. (dec.)
 (ii) Elemental analysis
 Calculated for $C_{21}H_{24}N_4O_3 \cdot H_2O$: C 63.30%; H 6.58%; N 14.06%.
 Found: C 63.5%; H 6.6%; N 14.1%.

The following compounds were obtained by substantially the same procedures as described in Examples 1–7.

2-(n-Propyl)-5-hydroxy-1H-imidazole-4carboxamide m.p. 251.5°–253.5° C. (dec.)

2-(iso-Propyl)-5-hydroxy-1H-imidazole-4-carboxamide m.p. 266.5°–267.5° C. (dec.)

2-(tert-Butyl)-5-hydroxy-1H-imidazole-4-carboxamide m.p. 304° C.

2-(n-Heptadecyl)-5-hydroxy-1H-imidazole-4-carboxamide m.p. 240.5°–243.5° C. (dec.)

2-Cyclopropyl-5-hydroxy-1H-imidazole-4-carboxamide m.p. 271° C. (dec.)

2-Cycloheptyl-5-hydroxy-1H-imidazole-4-carboxamide m.p. 276.5°–278° C. (dec.)

2-(1-Adamantyl)-5-hydroxy-1H-imidazole-4-carboxamide m.p. 310°–315° C. (dec.)

2-(3-Methoxybenzyl)-5-hydroxy-1H-imidazole-4-carboxamide m.p. 251°–256° C. (dec.)

2-(2-Methoxybenzyl)-5-hydroxy-1H-imidazole-4-carboxamide m.p. 273°–275° C. (dec.)

2-(4-Chlorobenzyl)-5-hydroxy-1H-imidazole-4-carboxamide m.p. 295°–300° C. (dec.)

2-(4-Nitrobenzyl)-5-hydroxy-1H-imidazole-4-carboxamide m.p. 307°–308° C. (dec.)

2-(4-Methylphenyl)-5-hydroxy-1H-imidazole-4-carboxamide m.p. 305°–311° C. (dec.)

(2-(3-Methylphenyl)-5-hydroxy-1H-imidazole-4-carboxamide m.p. 275°–280° C.

2-(4-Nitrophenyl)-5-hydroxy-1H-imidazole-4-carboxamide m.p. 326° C. (dec.)

2-(3-Nitrophenyl)-5-hydroxy-1H-imidazole-4-carboxamide m.p. 315°–320° C. (dec.)

2-(4-methoxyphenyl)-5-hydroxy-1H-imidazole-4-carboxamide m.p. 293°–301° C. (dec.)

2-(4-Carboxyphenyl)-5-hydroxy-1H-imidazole-4-carboxamide m.p. 317°–320° C.

2-(3-Carboxyphenyl)-5-hydroxy-1H-imidazole-4-carboxamide m.p. 349°–355° C. (dec.)

2-(3-Chlorophenyl)-5-hydroxy-1H-imidazole-4-carboxamide m.p. 298°–303° C. (dec.)

2-(4-Bromophenyl)-5-hydroxy-1H-imidazole-4-carboxamide m.p. 301°–303° C. (dec.)

2-(3-Bromophenyl)-5-hydroxy-1H-imidazole-4-carboxamide m.p. 303°–310° C. (dec.)

2-(3-Trifluoromethylphenyl)-5-hydroxy-1H-imidazole-4-carboxamide m.p. 293° C. (dec.)

2-(4-Benzoyloxyphenyl)-5-hydroxy-1H-imidazole-4-carboxamide m.p. 279°–281° C. (dec.)

2-(4-Ethoxycarbonylphenyl)-5-hydroxy-1H-imidazole-4-carboxamide m.p. 285°–293° C. (dec.)

2-(3-Ethoxycarbonylphenyl)-5-hydroxy-1H-imidazole-4-carboxamide m.p. 303°–310° C. (dec.)

2(4-Phenoxycarbonylphenyl)-5-hydroxy-1H-imidazole-4-carboxamide m.p. 283°–287° C. (dec.)

2-(3-Phenoxycarbonylphenyl)-5-hydroxy-1H-imidazole-4-carboxamide m.p. 296°–300° C. (dec.)

2-(4-Benzoylaminophenyl)-5-hydroxy-1H-imidazole-4-carboxamide m.p. 285°–290° C. (dec.)

2-[4-(N-Phenyl)-carbamoylphenyl]-5-hydroxy-1H-imidazole-4-carboxamide m.p. >360° C.

2-[3-(N-Phenyl)-carbamoylphenyl]-5-hydroxy-1H-imidazole-4-carboxamide m.p. 319°–322° C. (dec.)

2-(4-Carbamoylphenyl)-5-hydroxy-1H-imidazole-4-carboxamide m.p. 330°–335° C. (dec.)

2-(1,1-Diphenylmethyl)-5-hydroxy-1H-imidazole-4-carboxamide m.p. 270°–274° C.

EXAMPLE 8

A mixture of 3-nitrobenzonitrile (7.41 g), sodium methoxide (270 mg) and anhydrous methanol (35 g) was stirred at room temperature for 4 hours to give methanolic solution of methylimino 3-nitrobenzoate. To this solution were added acetic acid (3.6 ml), aminomalonamide (3.51 g) and anhydrous methanol (40 ml) and the mixture was stirred for 3.5 hours under reflux. After cooling to 0°–5° C., the precipitated product was separated from the solution by filtration, washed with ethanol and isopropylether, and dried under vacuum to give 2-(3-nitrophenyl)-5-hydroxy-1H-imidazole-4-carboxamide (6.67 g). The IR spectrum of this compound was identical with that of the product obtained by the manner similar to that described in Example 3.

The following compound was obtained in the same manner as described in Example 8.

2-(2-Nitrophenyl)-5-hydroxy-1H-imidazole-4-carboxamide m.p. 239°–242° C.

EXAMPLE 9

A mixture of 2-cyanopyridine (5.21 g), sodium methoxide (270 mg) and anhydrous methanol (35 g) was stirred at room temperature for 3.3 hours to give methanolic solution of methyl imino picolinate. To this solution were added acetic acid (3.6 ml), aminomalonamide (3.51 g) and anhydrous methanol (40 ml) and the mixture was stirred for 3 hours under reflux. After cooling to 0°–5° C., the precipitated product was separated from the solution by filtration, washed with ethanol and isopropylether, and dried under vacuum to give pale yellow crystalline (6.01 g) of 2-(2-pyridyl)-5-hydroxy-1H-imidazole-4-carboxamide. Recrystallization from aqueous methanol gave slightly yellowish fine needles.

(i) m.p. 276°–278° C. (dec.)

(ii) Elemental analysis

Calculated from $C_9H_8N_4O_2 \cdot \frac{1}{2}H_2O$: C 52.36% H 4.03%; N 27.14%.

Found: C 52.4%; H 4.2%; N 26.7%.

EXAMPLE 10

A mixture of 4-cyanopyridine (5.21 g), sodium methoxide (2.70 mg) and anhydrous methanol (35 g) was stirred at room temperature for 2.7 hours to give methanolic solution of methyl imino isonicotinate. To this solution were added acetic acid (3.6 ml), aminomalonamide (3.51 g) and anhydrous methanol (40 ml) and the mixture was stirred for 3 hours under reflux. In the course of the reaction, methanol (50 ml) was added again. After cooling to 0°–5° C., the precipitate was separated from the solution by filtration, washed with ethanol and isopropylether, and dried under vacuum to give yellow crystalline (5.76 g) of 2-(4-pyridyl)-5-hydroxy-1H-imidazole-4-carboxamide. Recrystallization from aqueous methanol gave dark yellow fine plates.

(i) m.p. 355° C.<

(ii) Elemental analysis

Calculated for $C_9H_8N_4O_2$: C 52.94%; H 3.95%; N 27.44%.

Found: C 52.6%; H 4.0%; N 27.8%.

The following compound was obtained in the same manner as described in Examples 9 and 10.

2-(3-Pyridyl)-5-hydroxy-1H-imidazole-4-carboxamide m.p. 299°–303° C.

EXAMPLE 11

To a suspension of aminomalonamide (7.13 g) in anhydrous ethanol (240 ml) were added triethyl orthopropionate (42.93 g) and concentrated sulfuric acid (1.6 g). The reaction mixture was refluxed for 2 hours and then ice-cooled. The precipitate product was filtered and washed with ethanol, isopropylether to give 2-ethyl-5-hydroxy-1H-imidazole-4-carboxamide (6.02 g).

(i) m.p. 255° C. (dec.)
(ii) Elemental analysis
Calculated for $C_6H_9N_3O_2$: C 46.44%; H 5.85%; N 27.08%.
Found: C 46.2%; H 5.85; N 26.8%.

EXAMPLE 12

A mixture of aminomalonamide (586 mg), triethyl orthobenzoate (5.61 g), concentrated sulfuric acid (100 mg) and anhydrous ethanol (20 ml) was stirred for 1.5 hours under reflux. After cooling to 0°–5° C., the precipitated product was separated by filtration, washed with ethanol, isopropylether and dried under vacuum to give colorless crystal. The IR spectrum and melting point of this compound were identical with that of the product obtained by the same procedure as Example 3.

EXAMPLE 13

A mixture of aminomalonamide (586 mg), triethyl ortho-p-chlorobenzoate (6.47 g), concentrated sulfuric acid (100 mg) and anhydrous ethanol (20 ml) was stirred for 1.5 hours under reflux. The resulting mixture was cooled to 0°–5° C., and the precipitated crystal was separated by filtration, washed with ethanol, isopropylether and dried under vacuum to give slightly yellowish crystal. The IR spectrum and melting point of this compound were identical with that of the product obtained by the same procedure as Example 5.

EXAMPLE 14

To a chilled suspension of 2-(4-benzoyloxyphenyl)-5-hydroxyimidazole-4-carboxamide (323 mg) in anhydrous methanol (20 ml) was added sodium methoxide (216 mg). After stirring for 5 minutes at 0°–5° C. and 15 minutes at room temperature, N-hydrochloric acid aqueous solution (4 ml) and isopropylether (30 ml) were added. The precipitated crystal was separated by filtration, washed with isopropylether and dried under vacuum to give 2-(4-hydroxyphenyl)-5-hydroxy-1H-imidazole-4-carboxamide (190 mg).

(i) m.p. 300°–304° C.
(ii) Elemental analysis
Calculated for $C_{10}H_9N_3O_3 \cdot \frac{1}{2}CH_3OH$:
C 53.61%; H 4.71%; N 17.87%.
Found: C 53.7%; H 4.3%; N 17.8%.

EXAMPLE 15

To a solution of 4-cyanopyridine N-oxide (600 g) in ahydrous methanol (250 ml) was added sodium methoxide (1.35 g), and this solution was stirred for 0.5 hour at room temperature. To this solution were added aminomalonamide (3.51 g) and acetic acid, and this mixture was stirred for 2 hours under reflux. After cooling the reaction mixture to 0°–5° C., the precipitated product was separated by filtration, washed with ethanol, isopropylether and dried under vacuum to give yellow crystal of 4-(4-carbamoyl-5-hydroxyimidazole-2yl)-pyridine-N-oxide (5.96 g).

(i) m.p. 318° C. (dec.)

(ii) Elemental analysis
Calculated for $C_9H_8N_4O_3 \cdot 1/5H_2O$: C 48.30%; H 3.78%; N 25.04%.
Found: C 48.0%; H 3.9%; N 25.1%.

The following compounds could be obtained by the procedure described in the present invention.

2-(2-Fluorophenyl)-5-hydroxy-1H-imidazole-4-carboxamide,
2-(3-Fluorophenyl)-5-hydroxy-1H-imidazole-4-carboxamide,
2-(4-Trifluoromethylphenyl)-5-hydroxy-1H-imidazole-4-carboxamide,
2-(iso-butyl)-5-hydroxy-1H-imidazole-4-carboxamide, and
2-(n-butyl)-5-hydroxy-1H-imidazole-4-carboxamide.

What is claimed is:

1. A compound selected from the group consisting of an amide of the formula

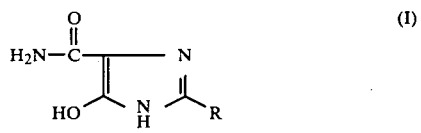

wherein R is (1) $C_3$-$C_7$ cycloalkyl, (2) 1-adamantyl, (3) pyridyl, (4) pyridine N-oxide, (5) diphenylmethyl, (6) benzyl which may or may not be substituted with nitro, halogen, $C_1$-$C_3$ alkyl or $C_1$-$C_3$ alkoxy, or (7) phenyl which may or may not be substituted with nitro, halogen, hydroxy, $C_1$-$C_3$ alkyl, $C_1$-$C_3$ alkoxy, carboxy, $C_2$-$C_4$ alkoxycarbonyl, phenoxycarbonyl, carbamoyl, N-phenylcarbamoyl, N-adamantylcarbamoyl, benzoylamino, trifluoromethyl, $C_2$-$C_4$ alkanoyloxy, 1-adamantoyloxy or benzoyloxy, and a non-toxic pharmaceutically acceptable salt of said amide.

2. A compound according to claim 1, wherein R is benzyl substituted with $C_1$-$C_3$ alkoxy, or phenyl substituted with halogen, $C_1$-$C_3$ alkoxy, N-adamantylcarbamoyl or 1-adamantoyloxy.

3. A compound according to claim 1, wherein R is 4-(1-adamantoyloxy)-phenyl.

4. A compound according to claim 1, wherein R is 4-chlorophenyl.

5. A compound according to claim 1, wherein R is 4-methoxybenzyl.

6. A compound according to claim 1, wherein R is 4-methoxyphenyl.

7. A compound according to claim 1, wherein R is 4-(N-adamantylcarbamoyl)-phenyl.

8. A compound according to claim 1, wherein R is 4-fluorophenyl.

9. A compound according to claim 1, wherein R is benzyl.

10. A compound according to claim 1, wherein R is phenyl.

11. A compound according to claim 1, wherein R is 4-nitrophenyl.

12. A compound according to claim 1, wherein R is 4-methylphenyl.

13. A compound according to claim 1, wherein R is 3-nitrophenyl.

14. A compound according to claim 1, wherein R is 4-pyridyl.

15. A compound according to claim 1, wherein R is 3-pyridyl.

16. A compound according to claim 1, wherein R is 4-(phenoxycarbonyl)-phenyl.

17. A compound according to claim 1, which is 4-(4-carbamoyl-5-hydroxy-1H-imidazole-2-yl)-pyridine-N-oxide.

18. A pharmaceutical composition useful as an immunostimulant, or as an anticancer agent against Sarcoma 180, which comprises a pharmacologically effective amount of a compound of claim 1 as an active ingredient, and a pharmaceutically acceptable carrier therefor.

19. A compound of the formula

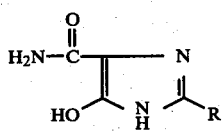

wherein R is $C_3$–$C_{17}$ alkyl, or a non-toxic pharmaceutically acceptable salt thereof.

20. A pharmaceutical composition useful as an immunostimulant, or as an anticancer agent against Sarcoma 180, which comprises a pharmacologically effective amount of a compound of claim 19 as an active ingredient, and a pharmaceutically acceptable carrier therefor.

21. 2-(n-Heptadecyl)-5-hydroxy-1H-imidazole-4-carboxamide, or a non-toxic pharmaceutically acceptable salt thereof.

22. 2-(n-Propyl)-5-hydroxy-1H-imidazole-4-carboxamide, or a non-toxic pharmaceutically acceptable salt thereof.

23. 2-(iso-Propyl)-5-hydroxy-1H-imidazole-4-carboxamide, or a non-toxic pharmaceutically acceptable salt thereof.

24. 2-(tert-Butyl)-5-hydroxy-1H-imidazole-4-carboxamide, or a non-toxic pharmaceutically acceptable salt thereof.

25. 2-(iso-Butyl)-5-hydroxy-1H-imidazole-4-carboxamide, or a non-toxic pharmaceutically acceptable salt thereof.

26. 2-(n-Butyl)-5-hydroxy-1H-imidazole-4-carboxamide, or a non-toxic pharmaceutically acceptable salt thereof.

* * * * *